United States Patent
Kuracina et al.

Patent Number: 6,156,010
Date of Patent: Dec. 5, 2000

[54] METHOD AND APPARATUS FOR INTRODUCING AN INTRAVENOUS CATHETER

[75] Inventors: Thomas C. Kuracina; Randall E. Ohnemus, both of Ventura, Calif.

[73] Assignee: Injectimed, Inc., Ventura, Calif.

[21] Appl. No.: 09/099,114

[22] Filed: Jun. 17, 1998

Related U.S. Application Data

[60] Provisional application No. 60/049,881, Jun. 17, 1997, and provisional application No. 60/055,366, Aug. 11, 1997.

[51] Int. Cl.$^7$ .......................... A61M 5/178; A61M 5/00; A61M 31/00; B65D 81/00

[52] U.S. Cl. .................. 604/168.01; 604/264; 604/507; 604/190; 604/187; 600/577; 600/579; 600/580

[58] Field of Search .................. 604/164, 264, 604/523, 187–88, 190, 218, 200–202, 240, 272, 167–69, 181; 600/573, 576–80, 167.02

[56] References Cited

U.S. PATENT DOCUMENTS

| | | | |
|---|---|---|---|
| 3,565,074 | 2/1971 | Foti et al. ................. | 604/164 |
| 3,749,084 | 7/1973 | Cucchiara ................. | 128/2 F |
| 4,269,186 | 5/1981 | Loveless et al. .......... | 128/214.4 |
| 4,313,440 | 2/1982 | Ashley ...................... | 128/218 R |
| 4,317,445 | 3/1982 | Robinson ................... | 604/264 |
| 4,767,407 | 8/1988 | Foran ........................ | 604/164 |
| 4,841,985 | 6/1989 | Wanamaker ............... | 128/763 |
| 4,904,240 | 2/1990 | Hoover ...................... | 604/53 |
| 4,917,671 | 4/1990 | Chang ....................... | 604/168 |
| 4,978,339 | 12/1990 | Labouze et al. ........... | 604/110 |
| 5,013,304 | 5/1991 | Russell et al. ............. | 604/167 |
| 5,032,116 | 7/1991 | Peterson et al. ........... | 604/168 |
| 5,117,837 | 6/1992 | Wanamaker et al. ...... | 128/763 |
| 5,151,087 | 9/1992 | Jonkman ................... | 604/164 |
| 5,250,030 | 10/1993 | Corsich .................... | 604/110 |
| 5,376,071 | 12/1994 | Henderson ................ | 604/169 |
| 5,514,100 | 5/1996 | Mahurkar .................. | 604/195 |
| 5,520,657 | 5/1996 | Sellers et al. ............. | 604/191 |
| 5,649,911 | 7/1997 | Terotola ................... | 604/164 |
| 5,755,701 | 5/1998 | Sarstedt .................... | 604/264 |
| 5,824,001 | 10/1998 | Erskine .................... | 604/158 |

FOREIGN PATENT DOCUMENTS 9812683  10/1998  WIPO .

*Primary Examiner*—Glenn K. Dawson
*Assistant Examiner*—Patricia M. Bianco
*Attorney, Agent, or Firm*—Stetina Brunda Garred & Brucker

[57] ABSTRACT

A method an apparatus for introducing an intravenous catheter. In one embodiment, a catheter having a flashback chamber is provided, the flashback chamber having a proximal end, a distal end and an inner wall. The distal end of the flashback chamber being in fluid communication with the catheter needle. A moveable member within the flashback chamber sealingly engages with the inner wall of the flashback chamber, the member being movable within the flashback chamber in a direction from the distal end to the proximal end of the flashback chamber. The movement of the member creates a vacuum within the flashback chamber.

18 Claims, 6 Drawing Sheets

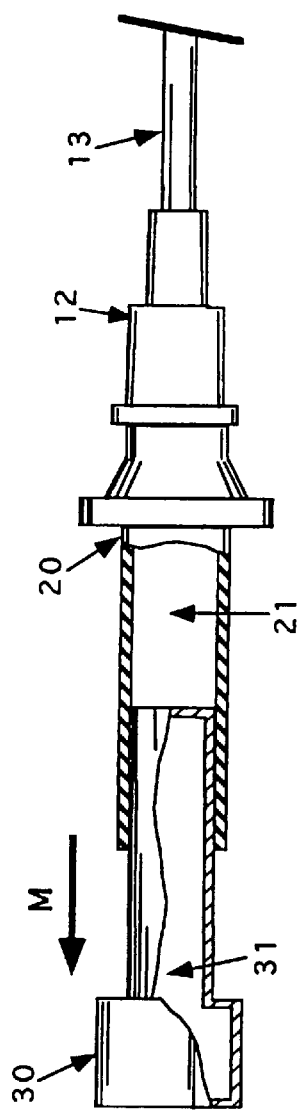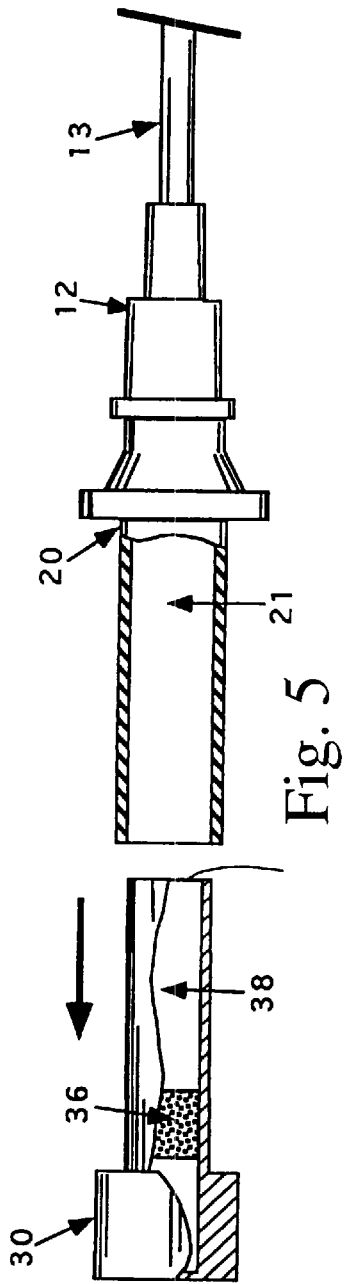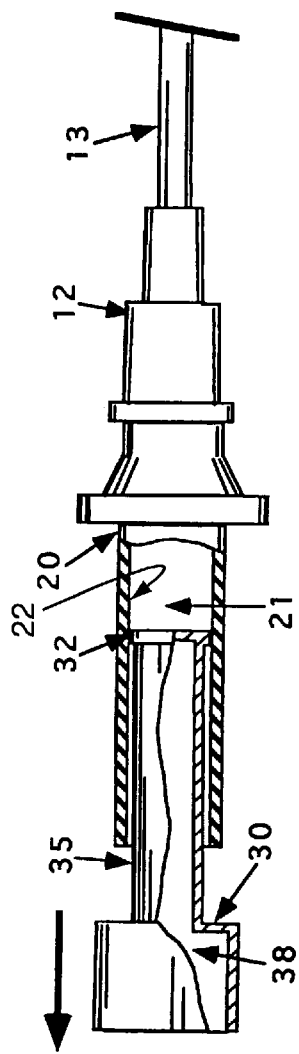

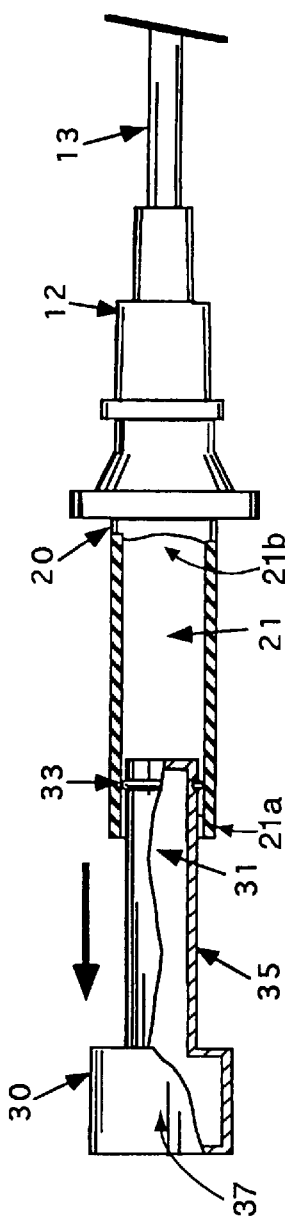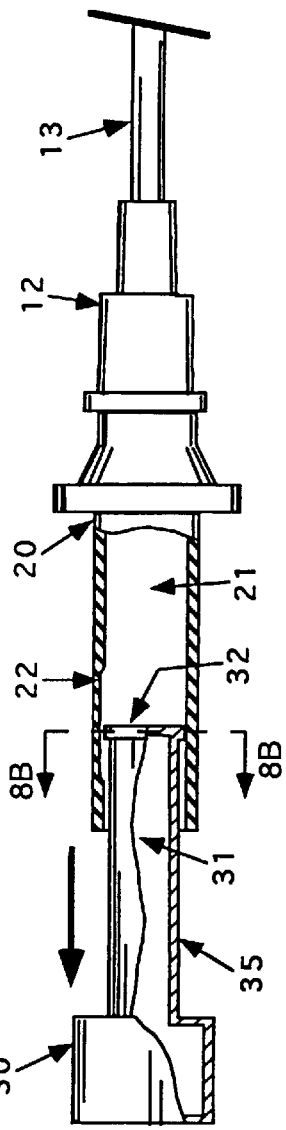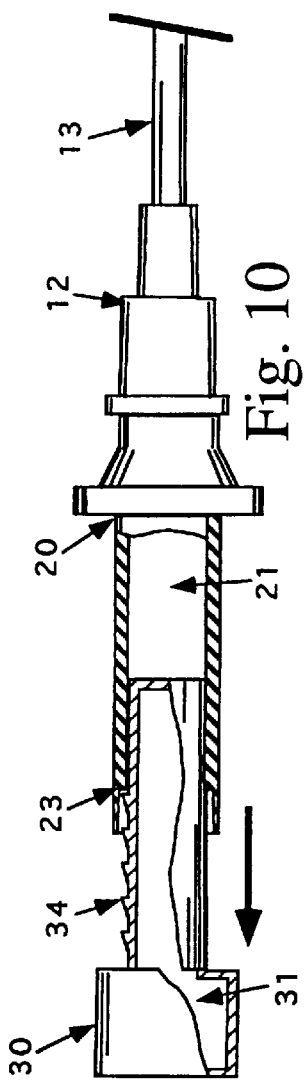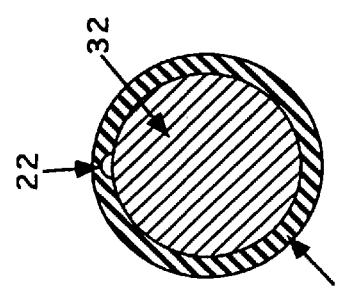

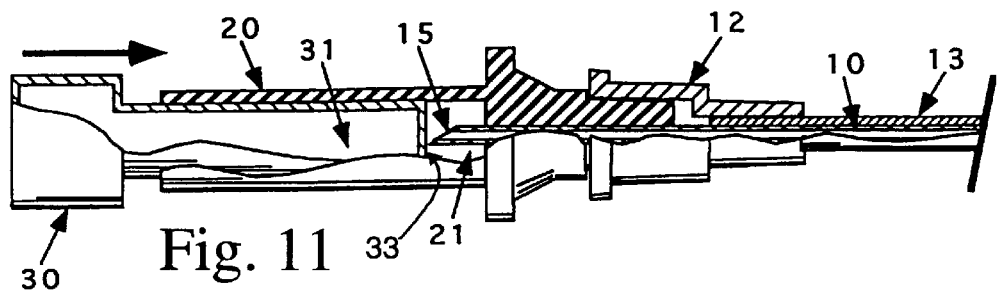
Fig. 11
Fig. 9A
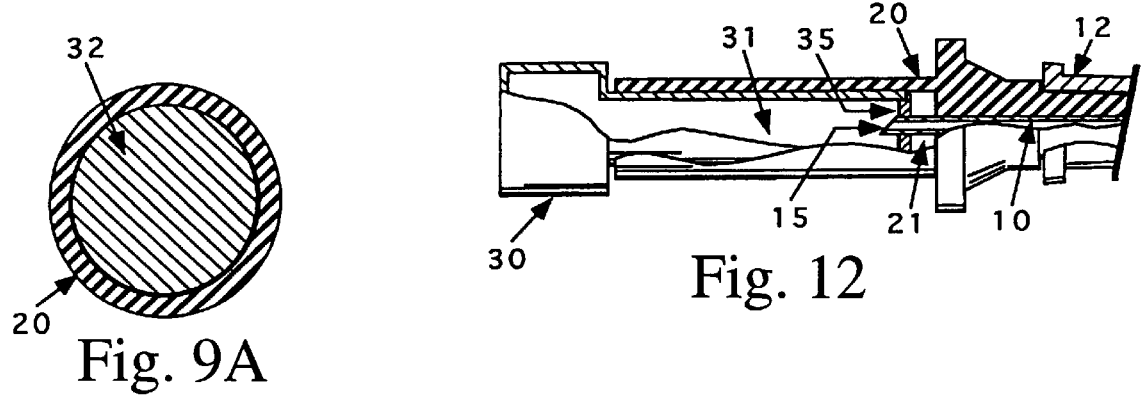
Fig. 12
Fig. 9B
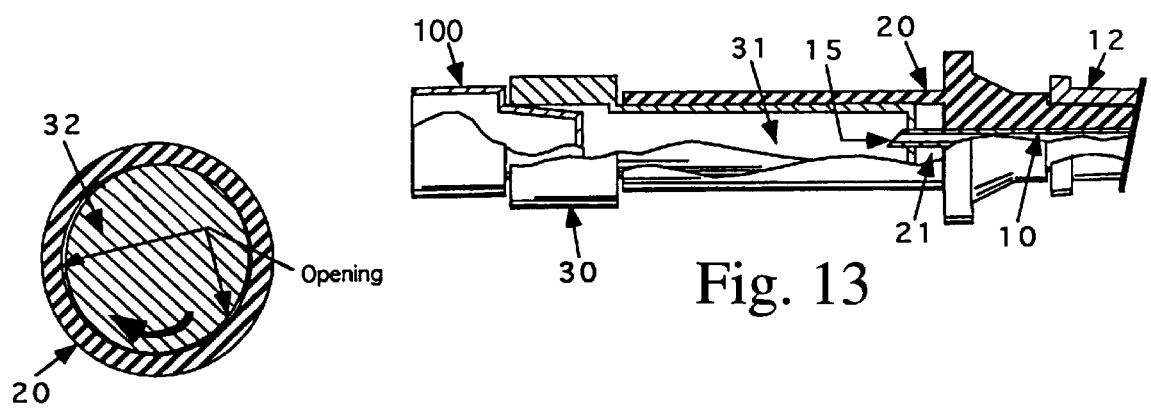
Fig. 13
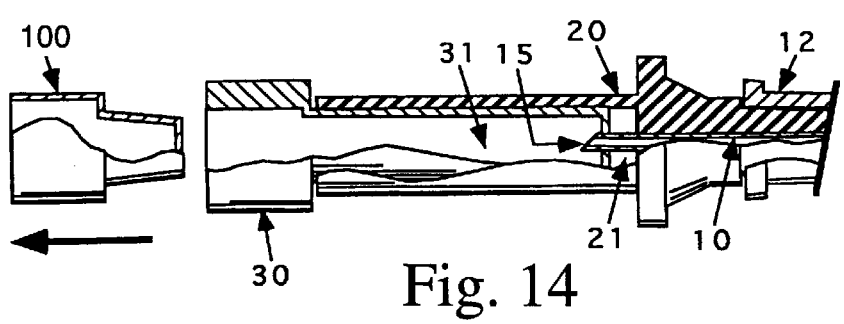
Fig. 14

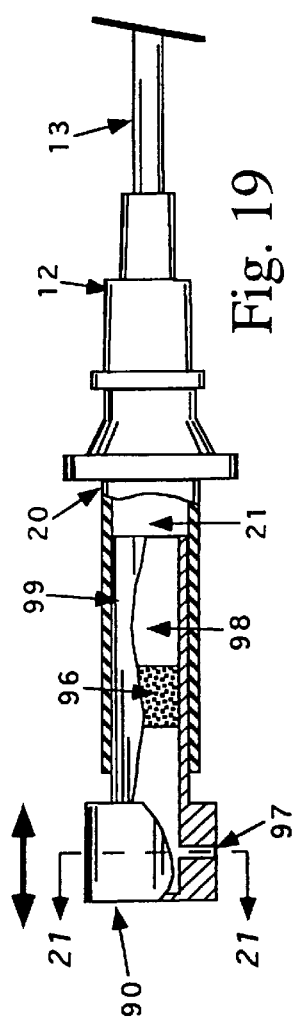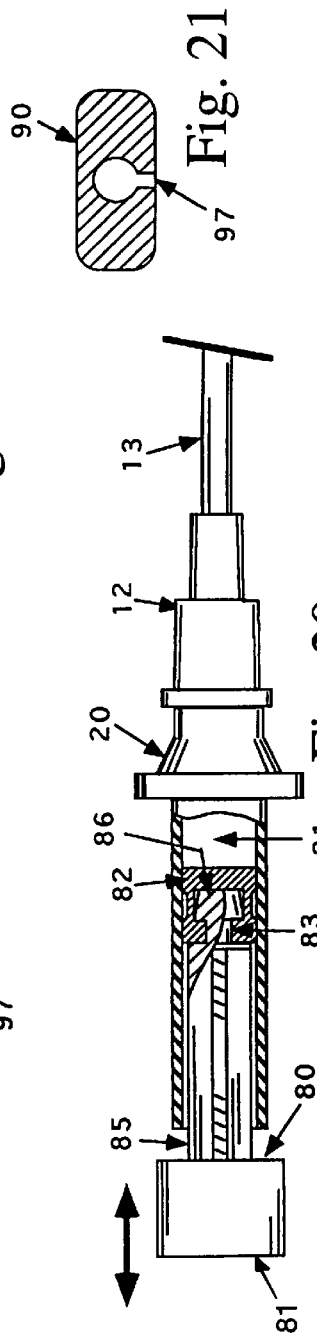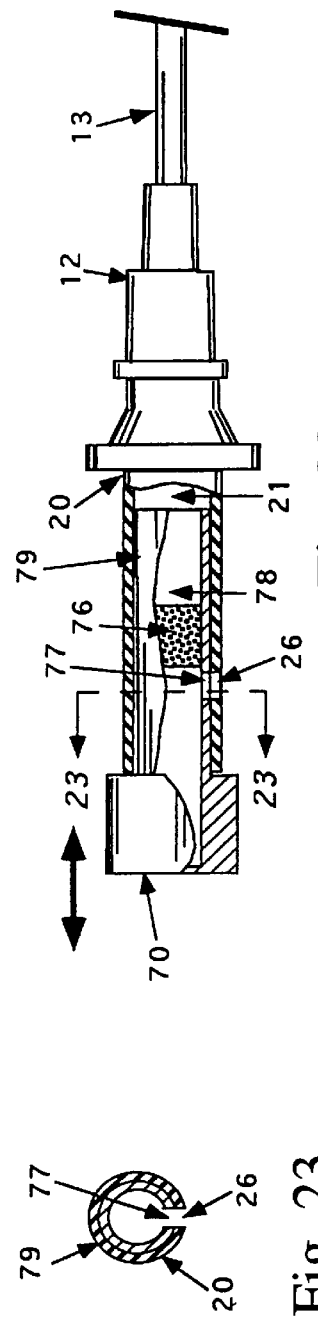

METHOD AND APPARATUS FOR INTRODUCING AN INTRAVENOUS CATHETER

RELATED APPLICATION

This application is related to and claims the benefit of the filing dates of the following United States Provisional Patent Applications: (1) METHOD AND APPARATUS FOR INTRODUCING AN INTRAVENOUS CATHETER, Ser. No. 60/049,881, filed Jun. 17, 1997, now abandoned and (2) METHOD AND APPARATUS FOR ACCELERATING FLASHBACK RESPONSE TIME IN AN INTRAVENOUS CATHETER, Ser. No. 60/055,366, filed Aug. 11, 1997, now abandoned.

FIELD OF THE INVENTION

The present invention relates generally to a method and apparatus for the introducing a peripheral Intravenous (I.V.) catheter, and more particularly to an I.V. catheter introducer with a suctioning means for aspirating fluid or gaseous substances through the needle during catheter placement procedures.

BACKGROUND OF THE INVENTION

Standard I.V. catheters are regularly used to infuse fluids into the bloodstream for medical purposes. In order to gain access to the bloodstream, a hollow tube or catheter must be placed within a blood vessel.

An I.V. catheter normally comprises a hollow bore needle with a sharpened distal end with the opposite, or proximal, end attached to a needle hub, with the proximal end of the needle being in communication with a hollow or "flashback" chamber of the needle hub, a separable flash plug sealingly closing the hollow chamber of the needle hub, and a separable catheter and catheter hub axially located about the needle.

A standard I.V. catheter is introduced into a blood vessel by means of a hollow bore needle whereby the catheter is placed axially on the needle and the sharp needle tip projects slightly beyond the distal end of the catheter. The sharp needle is used to pierce the skin and underlying tissue until the distal end of the catheter and needle enter the lumen, or fluid passageway, of the blood vessel. At this point, blood flows through the hollow bore of the needle and into the flashback chamber of the needle hub, indicating the catheter can be advanced into the blood vessel. At this point, the needle is held in a stationary position and the catheter is manually advanced into the blood vessel. When the catheter is properly inserted, manual pressure is placed on the catheter tube in the blood vessel to prevent blood from squirting out through the hollow bore of the catheter and the needle is withdrawn. A properly prepared and filled I.V. line is then attached to the catheter hub by an I.V. connector.

During the normal course of I.V. catheter placement, blood commonly fails to flow into the flashback chamber of the needle hub. This presents problems for both the healthcare worker and patient. In the current managed care environment, cost constraints place additional pressure on the healthcare worker to perform procedures safely, quickly and in a cost effective manner. The patient needs to be infused and the healthcare worker needs to complete the procedure and attend to the next task or patient. When blood fails to flow into the flashback chamber, the healthcare worker will most likely "fish" around with the I.V. catheter needle trying to properly locate the blood vessel. Many times this type of exploration is quite painful to the patient and may leave the patient's body tissue badly bruised and cut. Even after "fishing" to locate the blood vessel, blood still may not flow into the flash chamber of the needle hub.

The next step requires the healthcare worker to remove the flash plug from the needle hub and connect a sterile syringe to the proximal end of the needle hub. The syringe is used to create a suction, or sub-atmospheric pressure, within the hollow bore needle and flash chamber in hopes that blood will flow into the flashback chamber.

The healthcare worker must awkwardly attempt to keep the sharpened needle tip stationary in the patient while pushing the syringe toward the patient to maintain an airtight seal on the I.V. catheter needle hub, yet pull the syringe plunger rod away from the patient to create a suction within the inner chamber of the syringe and needle hub. Once blood appears in the flash chamber, the catheter usually can be advanced.

FIG. 1 illustrates a full and cross-sectional view of a prior art I.V. catheter introducer 140 that is used to place an I.V. catheter 113 into a blood vessel. The prior art I.V. catheter device has four primary components. These include: (1) a hollow bore needle 110 having a sharpened distal tip 111, with the proximal end of the needle 110 being fixedly attached to (2) a needle hub 120 with a hollow or "flashback" chamber 121 being in communication with the hollow bore of the needle 110, (3) a separable cap or "flash plug" 130 sealingly seated at the proximal end of the needle hub 120 creating the sealed, or vented, inner chamber 121, and (4) a separable catheter 113 attached to a catheter hub 112, catheter 113 axially surrounding the hypodermic needle 110.

FIG. 2 is a full and cross sectional view of a prior art I.V. catheter introducer and separable catheter shown in FIG. 1 having separable flash plug 130 being removed from needle hub 120. Flash plug 130 may also comprise an aperture or through hole which acts as a vent connecting the flashback chamber with the ambient atmosphere, said flash plug 130 having a filter membrane within which allows gaseous substances to pass through, but substantially prevents fluids from passing through said filter.

What is needed is an apparatus and method for introducing an I.V. catheter which does not at first require the use of another device, such as a syringe, to aspirate fluid or gaseous substances through the catheter needle and solves the aforementioned problems.

SUMMARY OF THE INVENTION

Wherefore, it is an object of this invention to provide an I.V. catheter introducer having a suctioning means for aspirating fluids through the needle.

It is an object of this invention to provide an I.V. catheter introducer having a suctioning means whereby the suctioning is created by a movable component.

It is an additional object of this invention to provide an I.V. catheter introducer having a suctioning means whereby the suctioning is created using no components other than those now comprising the standard I.V. catheter introducer.

It is another object of this invention to provide an I.V. catheter introducer having a suctioning means which looks similar to a standard, I.V. catheter introducer, that is, the flash plug is separable from the catheter needle hub.

It is another object of this invention to provide an I.V. catheter introducer having a suctioning means which conforms to existing procedures for introducing an I.V. catheter and allows unrestricted access for vascular procedures or I.V. catheter insertion.

It is yet another object of this invention to provide an I.V. catheter introducer having a suctioning means which provides an exposed sharpened tip for bevel-up needle viewing.

It is still another object of this invention to provide an I.V. catheter introducer having a suctioning means which automatically creates a sub-atmospheric pressure within the flashback chamber of the needle hub or within the flash plug.

It is a further object of this invention to provide an I.V. catheter introducer having a suctioning means which allows medication or diluent to be aspirated into and/or from a syringe.

It is still further an object of the invention to provide an I.V. catheter introducer having a suctioning means which can be used with a double lancet needle for piercing a movable flash plug or evacuated chamber.

It is an additional object of this invention to provide an I.V. catheter introducer having a suctioning means which lends itself to automated manufacturing.

It is a further object of the invention to reduce the number of components to the lowest possible number needed to accomplish the intended task of providing acceptable, low cost, single-use, I.V. catheter introducer for the healthcare industry.

It is an additional object of this invention to provide an I.V. catheter introducer having a suctioning means which allows a one-way axial movement of the flash plug.

It is another object of this invention to provide an I.V. catheter introducer having a suctioning means with a venting means to equalize the atmospheric and/or hydraulic pressure within the flash chamber or flash plug with the ambient atmospheric pressure when a suctioning force is applied, or when desired.

It is yet an additional object of this invention to provide an I.V. catheter introducer having a suctioning means which maintains a suctioning force within the flash chamber when the chamber has uneven or tapered sides.

It is still a further object of this invention to provide an I.V. catheter introducer having a suctioning means with an adjustable sealing means which self adjusts as the flash plug is moved.

It is yet another object of the invention to provide an I.V. catheter introducer having a suctioning means which is self-adjusting with the ambient atmospheric pressure.

It is still another object of the invention to provide an I.V. catheter introducer having a suctioning means which is self-adjusting as the flash plug is moved back or forth during use.

It is another object of the invention to have a flash plug which is axially moveable toward and away from the needle.

It is another object of this invention to provide an I.V. catheter introducer having a venting means to allow the air within the flashback chamber to be expelled when blood enters the flashback chamber.

It is a further object of the invention to provide a catheter introducer with a vent which can be opened or closed by axial or rotational movement of a flash plug relative to the introducer.

For simplicity sake, the numbered elements shown herein might be interchanged throughout the drawings on each different embodiment, whether the flash chamber or the flash plug, providing a variety of combinations of the described invention which would be obvious to anyone skilled in the art.

Other objects and benefits of this invention will become apparent from the description which follows hereinafter when read in conjunction with the drawing figures which accompany it.

The foregoing objects are achieved by the I.V. catheter introducing apparatus of the present invention capable of aspirating a fluid or gaseous substance through a hollow bore needle and chamber by: 1) creating a suction, or sub-atmospheric pressure, within the flashback chamber of an I.V. catheter needle hub, 2) creating a suction, or sub-atmospheric pressure, within the I.V catheter flash plug, 3) providing a flash plug having a sub-atmospheric pressure transferable to the flashback chamber of the needle hub, 4) a needle hub having a sub-atmospheric pressure transferable to the flashback chamber of the needle hub, 5) providing a suctioning flash plug having a means to vent air within the flashback chamber, or flash plug, when blood enters the flashback chamber, 6) providing a suctioning flash plug having a closable vent to create a sub-atmospheric pressure within the flashback chamber when desired, and 7) providing a suctioning flash plug having a closable vent to create a sub-atmospheric pressure within the flashback chamber when desired, with the closable vent being openable to create an equalized pressure within the flashback chamber when desired.

The invention provides a suctioning flash plug 30 which sealingly engages the hollow chamber 21 of the needle hub 20 whereby axial movement of the flash plug 30 creates a suction, or sub-atmospheric pressure within the flashback chamber 21. The suctioning flash plug 30 can be removed if necessary and a syringe can be connected to the needle hub 20 in the usual manner.

The invention relates to an I.V. catheter introducer having a built in suctioning means, or more particularly to an I.V. catheter introducer comprising a sharpened, hollow bore needle attached to a needle hub, with the proximal end of the needle being in connected to a hollow chamber of the needle hub, a flash plug, with a suctioning means, sealingly closing the hollow chamber of the needle hub, and a separable catheter and catheter hub axially located about the needle. Due to the universal application of the invention, a number of suctioning devices are described herein using the basic technology.

The embodiments disclosed herein all embody the "low-cost, high performance" criteria necessary to achieve an I.V. catheter with a flash plug capable of creating a suction within the hollow flash chamber, or within the flash plug itself, but are used the same way in practice as the standard I.V. catheter introducer is now used. In other words, the use of the suctioning flash plug becomes "transparent" to the existing procedure. This aspect of the invention is highly desirable because no change in technique, additional steps or equipment costs, are required to successfully introduce an I.V. catheter. This eliminates any additional material cost for additional equipment such as a syringe, and reduces the extra time required to locate the syringe, open the syringe package, connect the syringe to the needle hub and draw a vacuum within the needle hub, advance the catheter and dispose of the catheter needle, syringe, flash plug and packaging.

The present invention provides an improved apparatus and method for aspirating fluid or gaseous substances through a needle and into or through an I.V. catheter introducer flashback chamber or flash plug.

The present invention also provides an improved apparatus and method for accelerating flashback response time when introducing an I.V. catheter.

In one embodiment, a one piece flash plug sealingly engages the perimeter of the needle hub flash chamber and creates a suctioning, or sub-atmospheric pressure, in the flash chamber as the flash plug is axially moved away from the needle.

In one embodiment, a venting means equalizes the pressure within the hollow chamber of the needle hub with the ambient air pressure at a pre-determined position, or as needed.

In another embodiment, the flash plug is movable in only one direction.

In yet another embodiment, the flash plug has an adjustable sealing means for engaging a tapered, or unevenly shaped flash chamber.

In still another embodiment, the flash plug has a piercable, evacuated, or sub-atmospheric, pressure chamber.

In an additional embodiment, the flash plug has a venting means or separable cap for equalizing the atmospheric pressure within the flash chamber, or flash plug, with the ambient atmospheric pressure.

In another embodiment, the flash plug is removable for attaching a syringe to the flashback chamber of the needle hub.

In yet another embodiment, the flash plug has a removable or openable component for equalizing the atmospheric pressure within the flashback chamber, or flash plug, with the ambient atmospheric pressure.

In one embodiment, a vacuum can be created with in the flash plug while the flash plug is residing in the flash chamber.

In another embodiment, the flash plug has a self-adjusting means for equalizing the atmospheric and/or hydraulic pressure within the flashback chamber, or flash plug, with the ambient atmospheric pressure.

In yet another embodiment, an I.V. catheter needle hub has an evacuated chamber with a breakable or piercable membrane for creating a vacuum within the flashback chamber.

In one embodiment, a one piece flash plug sealingly engages the perimeter of the needle hub flash chamber and creates a suctioning, or sub-atmospheric pressure, in the flash chamber as the flash plug is axially moved away from the needle. A closable venting means is provided to allow the air within the flashback chamber to be easily displaced by the blood entering the chamber under normal insertion conditions when the distal end of the needle enters a blood vessel and blood flows through the needle and into the chamber. The vent can be blocked by placing a finger over the vent aperture. When the vent is blocked, and the flash plug is moved away from the needle, a sub-atmospheric pressure is created within the flashback chamber and hollow bore needle. A porous material which allows air, but not fluid, to pass through it can be included in the chamber of the flash plug. The material prevents blood from exiting the vent.

The user can easily equalize the sub-atmospheric pressure created within the hollow chamber of the needle hub with the ambient air pressure by simply unblocking the vent.

In another embodiment, the flash plug comprises a piston which sealingly engages the inner wall of the flashback chamber. The piston is attached to a plunger rod and frictionally engages the inner wall of the flashback chamber sufficient to hold the flash plug at any position along the length of the flashback chamber. All embodiment described herein can also have frictional engagement between the movable flash plug and flashback chamber perimeter sufficient to hold the flash plug at any position along the length of the flashback chamber.

The remaining disclosed embodiments all contribute to a better, more reliable and dependable product, serving the needs of healthcare workers and patients worldwide.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 4 illustrates a cut away view of the present invention with a flash plug being axially moved away from the needle hub.

FIG. 5 illustrates a cut away view of the present invention of a catheter introducer with a flash plug being separated from the needle hub.

FIG. 6 illustrates another embodiment of the present invention of a catheter introducer with a flash plug having a reduced diameter body.

FIG. 7 illustrates another embodiment of the present invention of a catheter introducer with a flash plug having a self-adjusting sealing means.

FIG. 8A illustrates another embodiment of the present invention of a catheter introducer with a flash plug and introducer having a venting means.

FIG. 8B illustrates a cross sectional view of the venting means of FIG. 8A.

FIG. 9A illustrates a cross sectional view of one embodiment of the invention with the flash plug sealingly engaging the perimeter of the flash back chamber.

FIG. 9B illustrates a cross sectional view of FIG. 9A with the flash plug rotationally moved to break the seal with the perimeter of the flash back chamber allowing passage of air or fluids.

FIG. 10 is another embodiment of the present invention of a catheter introducer with a flash plug having one way axial movement relative to the introducer.

FIG. 11 illustrates a catheter introducer with a double tipped needle having an evacuated flash plug in a ready to use configuration.

FIG. 12 illustrates a catheter introducer with the double tipped needle piercing the evacuated flash plug.

FIG. 13 illustrates a catheter introducer with the double tipped needle piercing the evacuated flash plug having a removable portion.

FIG. 14 illustrates a catheter introducer of FIG. 13 with the double tipped needle piercing the evacuated flash plug with the end cap removed.

FIG. 19 illustrates a side and cut away view of the present invention with an aspirating flash plug with a venting means and a porous material which allows air, but not fluid to pass through it.

FIG. 20 illustrates a side and cut away view of the present invention with an aspirating flash plug with separate piston.

FIG. 21 is a cross sectional view of one configuration of the proximal end of the aspirating flash plug with a venting means.

FIG. 22 illustrates a cross sectional and cut away view of the present invention with a vent through the side wall of the flash plug and needle hub.

FIG. 23 illustrates a cross sectional view of the venting area of FIG. 22.

DETAILED DESCRIPTION

A method and apparatus for introducing an intravenous catheter is described. In the following description, numerous specific details are set forth in order to provide a thorough understanding of the present invention. It will be apparent, however, to one skilled in the art that the present invention may be practiced without these specific details. In other instances, well-known components, structures and techniques have not been shown in detail in order to avoid obscuring the present invention.

Figure 1:
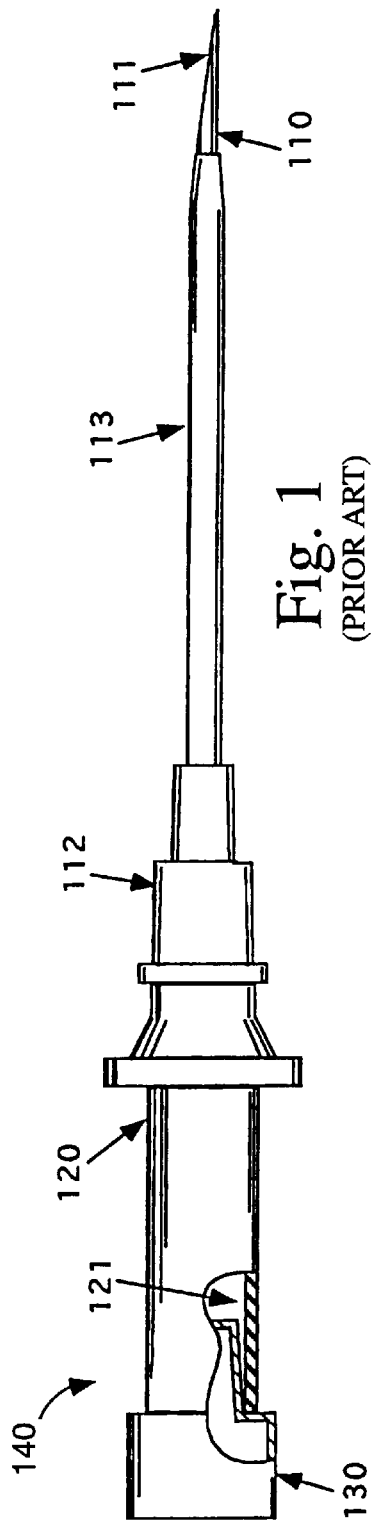
FIG. 1 illustrates a side and cut away view of a standard I.V. catheter and introducer ready to use.
Figure 2:
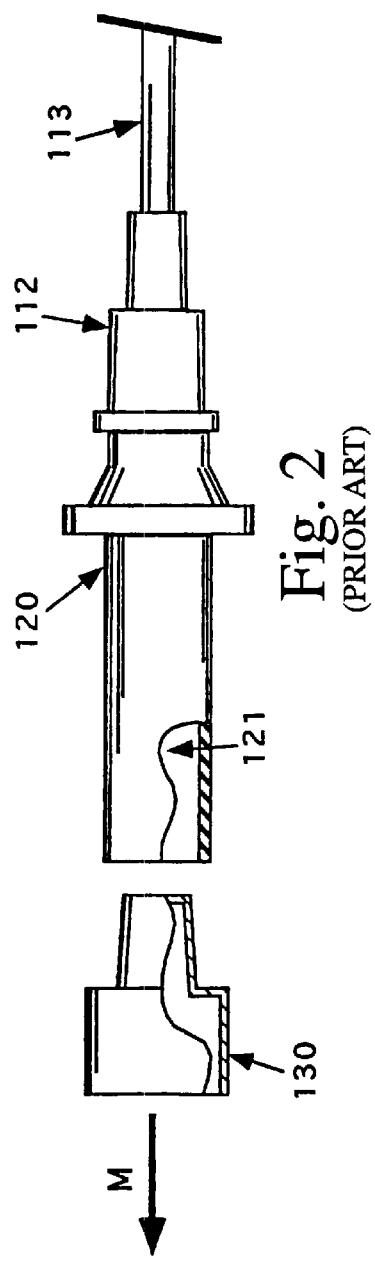
FIG. 2 illustrates a side and cut away view of a standard I.V. catheter and introducer with the flash plug separated from the introducer body.
Figure 3:
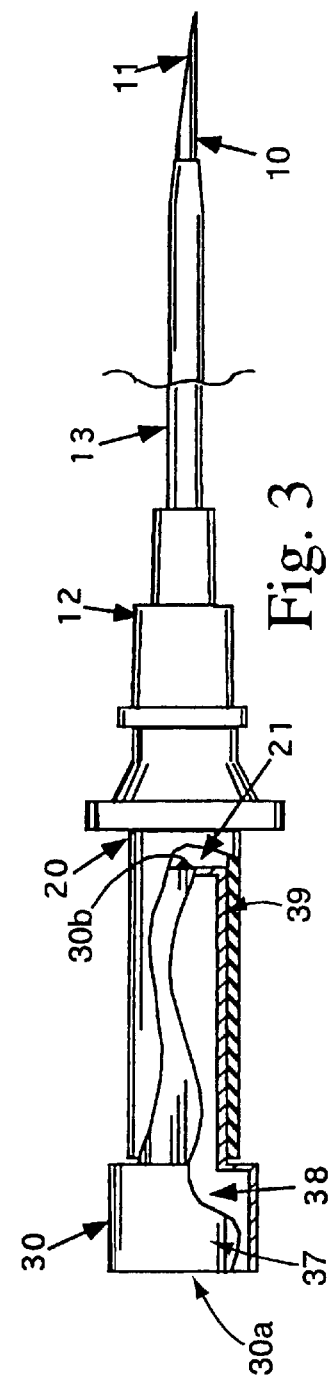
FIG. 3 illustrates a cut away view of the present invention ready to use with a flash plug residing within the needle hub.

FIG. 3 is a full and cross sectional view of an I.V. catheter introducer ready for use comprising a separable catheter 13 connected to hub 12, the catheter being slidably disposed on a hypodermic needle 10 which is fixedly attached to a needle hub 20. Needle hub 20 includes a flashback chamber 21 with a flash plug 30 residing at the proximal end of needle hub 20. A longitudinal body member 39 of flash plug 30 sealingly engages the perimeter of flashback chamber 21 creating a contained space within needle hub 20. Flash plug 30 can be removed by gripping the proximal end portion or flange portion 37 of the flash plug and moving the flash plug axially away from needle hub 20. Axial movement of the flash plug 30 in a direction from the distal end 21b to the proximal end 21a of the flashback chamber 21 causes a vacuum, or sub-atmosphereic pressure, to be created within the flashback chamber. In the embodiment of FIG. 3, flash plug 30 is axially movable toward and away from needle 10 and has an open proximal end 30a, a closed distal end 30b, and an open internal chamber 38. In an alternative embodiment, the proximal end 30a of flash plug 30 is closed to create a closed internal chamber. In yet another embodiment, flash plug 30 has a closed proximal end 30a and an open distal end 30b.

Throughout the description, the flashback chamber is described as being integral to the needle hub 20. It is appreciated, however, that the flashback chamber may be a separate component that is attached to the needle hub using well known techniques in the art. The present invention is aimed at providing a means in which a healthcare worker may manually create a vacuum in the flashback chamber. Therefore, it is appreciated that the present invention is not limited to the use of a moveable flash plug to create a vacuum in the flashback chamber. Any member or device that is capable of sealingly engaging the inner wall 22 of the flashback chamber 21 and being moveable in a direction from the distal end 21b to the proximal end 21a of the flashback chamber 21 may be used to create a vacuum within the flashback chamber.

In accordance with the teachings of the present invention, blood or other bodily fluids may be drawn into the flashback chamber 21 of the I.V. catheter by first introducing the distal end 11 of needle 10 into a vein or other body part and then moving the flash plug or other moveable sealing member located within the flashback chamber in a direction from the distal end to the proximal end of the flashback chamber to create a vacuum within the flashback chamber. In another embodiment, blood may be drawn into the flashback chamber by 1) introducing the distal end 11 of needle 10 into a portion of a body having a vein; 2) moving the flash plug or other moveable sealing member located in the flashback chamber in a manner so as to create a vacuum in the flashback chamber; and 3) introducing the distal end 11 of the needle 10 into the vein.

FIG. 4 is a full and cross sectional view of an I.V. catheter introducer similar to that shown in FIG. 3. The I.V. catheter includes a flash plug 30 that is capable of being axially moved (as indicated by arrow M) within needle hub 20 to create a vacuum, or sub-atmospheric pressure within flashback chamber 21. In the embodiment of FIG. 4. flash plug 30 has a closed internal chamber 31 and closed proximal and distal ends. The catheter 13 and catheter hub 12 will be shown but not described in the subsequent drawings of this application.

FIG. 5 is a full and cross sectional view of an I.V. catheter introducer similar to those shown in FIG. 3. The I.V. catheter includes a flash plug 30 having an open distal end 30b opening into an internal chamber 38. Figure shows flash plug 30 being separated from flashback region of the needle hub 20, thus opening the flashback chamber 21 to the ambient atmosphere. Flash plug 30 includes a fluid absorbing medium 36 located within internal chamber 38. The absorbing medium 36 acts to absorb blood or other fluids contained within the flashback chamber, thereby minimizing spillage of the fluids in the event the flash plug is removed from the flashback chamber. In one embodiment, flash plug 30 may include an aperture (not shown) located at, or near, the proximal end 30a of the flash plug. In this manner, the user may control the pressure in the flashback chamber 21 by moving the flash plug relative to the flashback chamber and venting the flashback chamber to the ambient atmosphere through the venting aperture as needed to maintain a desired pressure.

FIG. 6 is a full and cross sectional view of an I.V. catheter introducer similar to that shown in FIGS. 3, 4 and 5. The I.V. catheter includes a flash plug 30 that is axially movable within needle hub 20 to create a vacuum, or sub-atmospheric pressure within flashback chamber 21. Flash plug 30 has a section 35 which is dimensionally smaller than the flashback chamber 21 and form fitting section 32 for sealingly engaging the perimeter of flashback chamber 21. In the embodiment of FIG. 6, flash plug 30 has an open internal chamber 38. Flash plug 30 may also have a closed internal chamber.

FIG. 7 is a full and cross sectional view of an I.V. catheter introducer of another embodiment of the invention. The I.V. catheter includes a flash plug 30 that is axially movable within needle hub 20. Axial movement of the flash plug 30 in a direction from the distal end 21b to the proximal end 21a of the flashback chamber 21 causes a vacuum, or sub-atmospheric pressure, to be created within flashback chamber 21. Flash plug 30 has a longitudinal body or section 35 extending from a flange portion 37, the body 35 being dimensionally smaller than the flashback chamber 21. An o-ring 33, is positioned on the body 35 for sealingly engaging the perimeter of flashback chamber 21. O-ring 33 may comprise a rigid, semi-rigid, elastomeric, or a form fitting material. Flash plug 30 is shown having a closed, internal chamber 31, but may also include an open internal chamber.

FIG. 8 is a full and cross sectional view of an I.V. catheter introducer having a venting means 22. The flash plug 30 is shown being axially moved within needle hub 20 to create a vacuum, or sub-atmospheric pressure, within flashback chamber 21. Flash plug 30 has a flange portion 50 and a longitudinal body section 35, the longitudinal body section 35 being dimensionally smaller than the flashback chamber 21. A form fitting section 32 for sealingly engaging the perimeter of flashback chamber 21 is provided at the distal end of the flash plug. Needle hub 20 has at least one internal undercut, slot, passageway or vent 22 for equalizing the atmospheric pressure within the flashback chamber 21 with the ambient atmospheric pressure when form fitting section 32 engages vent opening or recess 22. In lieu, or in combination with vent opening 22, there may be a series of undercuts, located longitudinally or circumferentially, about the inner walls of needle hub 20 allowing suction to be repeated and relieved at various positions along the stroke of movable flash plug 30. The sub-atmospheric pressure created within flashback chamber 21 by the axial movement of the flash plug 30 is relieved or equalized with the ambient atmospheric pressure when sealing section 32 moves adjacent to passageway 22 allowing communication between the flashback chamber 21 and the outside ambient atmosphere. The passageway 22 could extend to proximal end of the needle hub 20.

In an embodiment wherein the venting passageway/recess/opening 22 is positioned at the inner most end of chamber 21, the form fitting section 32 at the distal end of flash plug 30 can be positioned in proximity to vent 22 such that when flash plug 30 is fully inserted, the air inside chamber 21 can be freely expelled through vent 22 when blood enters chamber 21 during normal flashback circumstances. A sub-atmospheric pressure can be created within flashback chamber 21 as flash plug 30 is moved axially away from needle hub 20. FIG. 8B is a cross-sectional view of needle hub 20, sealing section 32 and vent 22 in axis 8B—8B.

FIG. 9A is a cross-sectional view of another embodiment of the invention wherein the needle hub 20 has an elliptical or oval shape and sealing section 32 has a matching, or form fitting, elliptical or oval shape whereby axial movement of flash plug 30 maintains sealing engagement with inner wall of flash chamber 21.

As shown in FIG. 9B, the circumferential or rotational movement of flash plug 30 (as indicated by arrow R) and, hence, sealing section 32, causes the sealing section 32 to deform to create one or more openings or passageways. The existence of the openings causes the sub-atmospheric pressure within flash chamber 21 to equalize with outside ambient atmospheric pressure. This allows the healthcare worker to relieve the vacuum created within the flashback chamber 21 at any time during the aspiration procedure. By simply re-engaging form fitting sections of flash plug 32 and needle hub 20, an additional, or repeated sub-atmospheric pressure can be created within chamber 21.

FIG. 10 is a full and cross sectional view of an I.V. catheter introducer having a flash plug 30 that is axially movable within a needle hub 20 to create a vacuum, or sub-atmospheric pressure, within flashback chamber 21. A means for allowing one way axial movement of flash plug 30 is provided. In one embodiment, the means for restricting the movement of the flash plug in a direction from the proximal end to the distal end of the flashback chamber includes at least one projection or tooth 34 located on the outer wall of the flash plug and a recess 23 located on the needle hub 20 for engaging projection 34. Recess 23 is shown, but is not necessary to accomplish the limited axial movement of engaging projection 34. Flash plug 30 is shown having a closed, internal chamber 31, but may also include an open internal chamber.

FIG. 11 is a full and cross sectional view of an I.V. catheter introducer ready for use and having a flash plug 30 with a sub-atmospheric pressure within chamber 31 and a piercable distal end 33. Needle 10 has a sharpened proximal end 15 residing within flashback chamber 21 for piercing the distal end 33 of flash plug 30. Flash plug 30 sealingly engages the perimeter of flashback chamber 21 to create a contained space within needle hub 20. Piercable flash plug 30 is axially movable toward and away from needle tip 15. Flash plug 30 is shown with a closed proximal end and sealed internal chamber 31.

In the event that the healthcare worker fails to draw blood or fluid through the hollow bore needle when the evacuated flash plug pierces sharpened proximal needle tip 15, suction can still be created within flash chamber 21 by axially moving flash plug 30 away from needle 10. Flash plug 30 can be removed from needle hub 20 and a syringe can be attached to aspirate fluid or gaseous substances through or within chamber 31 and needle 10 if needed.

FIG. 12 is a full and cross sectional view drawing of an I.V. catheter introducer showing an evacuated flash plug 30 having a piercable sealing stopper or diaphragm 35 sealing the distal end of the flash plug. In FIG. 12, diaphragm 35 is shown being pierced by the sharpened proximal needle tip 15. Piercable flash plug 30 has a sub-atmospheric pressure chamber 31 sealed at one end by the stopper or diaphragm 35. Piercable flash plug 30 is axially movable toward and away from needle tip 15. Needle 10 has a sharpened proximal end 15 residing within flashback chamber 21 for piercing the diaphragm or stopper 35 at the distal end of flash plug 30. Flash plug 30 sealingly engages the perimeter of flashback chamber 21 creating a contained space within needle hub 20. Flash plug 30 shown with a closed proximal end. Flash plug 30 can be removed from needle hub 20 and a syringe can be attached to aspirate fluid or gaseous substances through or within the flashback chamber 21 and needle 10 if needed.

When distal needle tip 11 and catheter 13 are properly positioned within a blood vessel, and evacuated flash plug 30 is pierced by sharpened needle tip 15, fluid or gaseous substances are drawn through needle 10 and into chamber 31 indicating that the catheter is ready to be advance into the blood vessel.

FIG. 13 is a full and cross sectional view of an I.V. catheter introducer having an evacuated flash plug 30 that is piercable by the sharpened proximal needle tip 15 of a needle 10. Piercable flash plug 30 has an evacuated chamber 31 wherein the internal pressure may be equalized with the outside ambient atmospheric pressure by the removal of a second flash plug or end cap 100 that is in sealing engagement with an opening in the proximal end of flash plug 30. Piercable flash plug 30 is axially movable toward and away from needle tip 15. The sharpened proximal end 15 of needle 10 resides within flashback chamber 21 for piercing the distal end of flash plug 30. Flash plug 30 sealingly engages the perimeter of flashback chamber 21 to create a contained space within needle hub 20. When flash plug 30 is removed from needle hub 20, a syringe may be attached to aspirate fluid or gaseous substances through or within chamber 31 and needle 10 if needed. Chamber 31 could also include a porous material to allow air to pass through, but not fluids.

FIG. 14 is a full and cross sectional view of the I.V. catheter introducer shown in FIG. 13 with the evacuated flash plug 30 having been pierced by the sharpened proximal needle tip 15 of needle 10. The end cap 100 is also shown removed, thus allowing syringe attachment to flash plug 30

Figure 15:
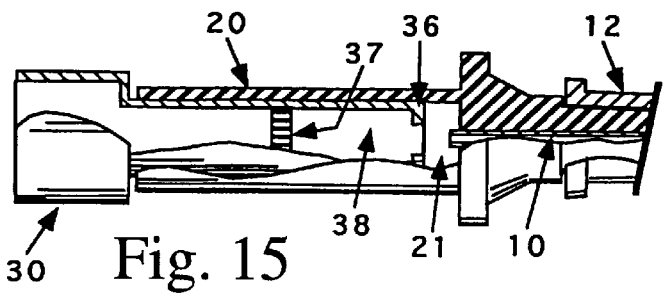
FIG. 15 illustrates a catheter introducer showing a self-adjusting or pressure equalizing flash plug in a ready to use configuration.

FIG. 15 is a full and cross sectional view of an I.V. catheter introducer shown in a ready for use configuration in another embodiment of the present invention. The I.V. catheter introducer is shown having a self-adjusting or pressure equalizing flash plug 30. Flash plug 30 sealingly engages the perimeter of flashback chamber 21 creating a contained space within needle hub 20. Flash plug 30 has a movable diaphragm 37 located within an internal chamber 38 of the flash plug. The axial position of diaphragm 37 changes, or self-adjusts in response to the internal pressure differential created by back or forth axial movement of flash plug 30. As flash plug 30 is moved away from needle 10, a sub-atmospheric or hydraulic vacuum is created within needle 10, chambers 21 and 38, drawing movable diaphragm 37 towards needle 10 and blood or fluid into hypodermic needle 10 and flash chambers 21 and 38.

Protrusion 36 on flash plug 30 limits axial movement of movable diaphragm 37 towards needle 10, allowing a steady atmospheric or hydraulic vacuum to be maintained within chambers 38 and 21 when flash plug 30 is moved an axial distance away from needle 10 and is held stationary. Additional sub-atmospheric or hydraulic vacuum can be created within chambers 21 and 38 by axially moving flash plug 30 farther away from needle 10. Conversely, atmospheric or hydraulic vacuum can be reduced or equalized by axially moving flash plug 30 toward needle 10. Movable diaphragm 37 allows blood entering flashback chamber 21 to be displaced under normal flashback circumstances and eliminates the need to vent air within chamber 21 as blood enters chamber 21.

Figure 16:
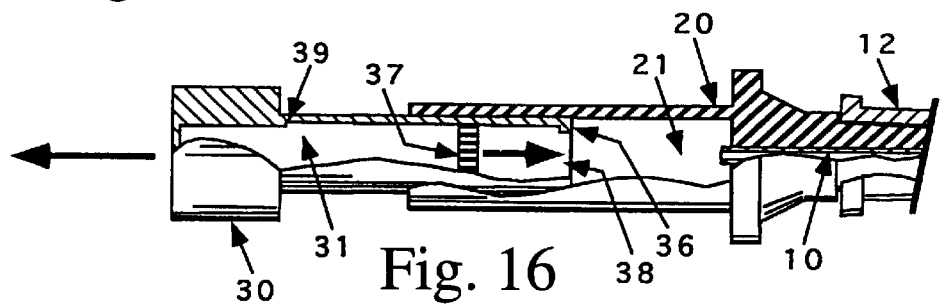
FIG. 16 illustrates a catheter introducer showing a self-adjusting or pressure equalizing flash plug being moved axially away from the needle hub.

FIG. 16 is a full and cross sectional view of an I.V. catheter introducer having a self-adjusting or pressure equalizing flash plug 30. Flash plug 30 sealingly engages the perimeter of flashback chamber 21 creating a contained space within needle hub 20. When flash plug 30 is axially moved away from needle 10, a sub-atmospheric or hydraulic vacuum is created within chambers 21 and 38, drawing movable diaphragm 37 towards needle 10 and aspirating fluid or gaseous substances through or into needle 10 and flash chambers 21 and 38. Protrusion 36 on flash plug 30 limits axial movement of movable diaphragm 37 towards needle 10, allowing a steady sub-atmospheric or hydraulic vacuum to be maintained within chambers 38 and 21 when flash plug 30 is moved an axial distance away from needle 10 and is held stationary. Flash plug 30 having a closed, sealed proximal end creating pressurized chamber 31 which compresses the gaseous substance contained within chamber 31 when flash plug 30 is axially moved toward needle 10.

Figure 17:
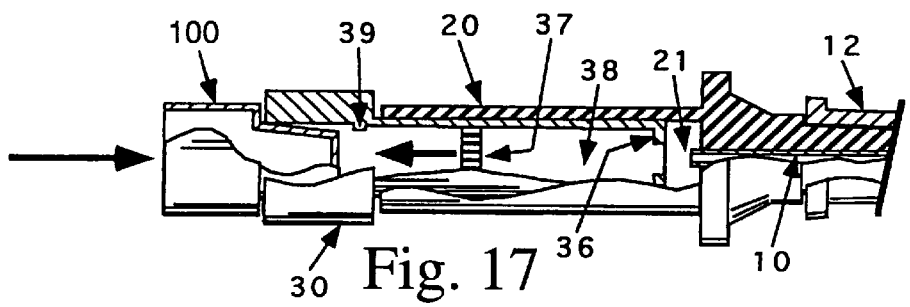
FIG. 17 illustrates a catheter introducer showing a self-adjusting or pressure equalizing flash plug with a removable end cap being moved axially toward the needle hub.
Figure 18:
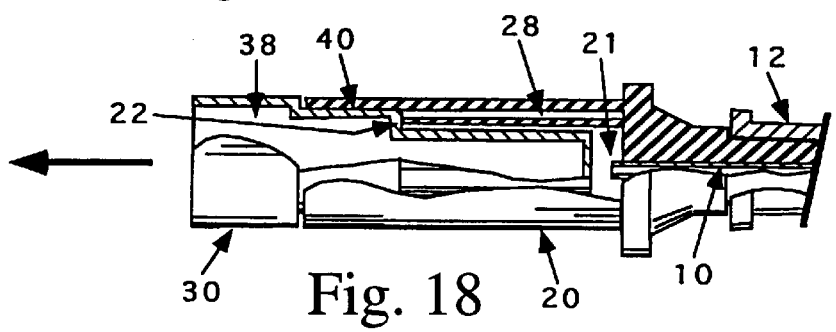
FIG. 18 illustrates a catheter introducer and flash plug with a needle hub having an evacuated portion.

As shown in FIG. 17, when flash plug 30 is axially moved toward needle 10, the sub-atmospheric or hydraulic vacuum within chambers 21 and 38 is reduced or equalized. This causes the movable diaphragm 37 to be moved in a direction away from needle. Internal pressure within needle 10, chambers 21 and 38 can be increased once chambers 21 and 38 are filled with fluid or gaseous substances and the flash plug 30 is moved toward needle 10. A protrusion 39 (also shown in FIG. 16.) on flash plug 30 limits axial movement of movable diaphragm 37 away needle 10, allowing injection of fluid or gaseous substances back through needle 10. As shown in FIG. 17, flash plug 30 may include a removable end cap 100 at its proximal end. The end cap 100 may be used as an additional means for venting or equalizing the pressure within the inner chamber 38 of flash plug 30., FIG. 18 is a full and cross sectional view of an I.V. catheter introducer having a suctioning means contained within a needle hub 20.

The needle hub 20 includes a plurality of chambers 28 and 21 with chamber 28 having a sub-atmospheric pressure. A portion of the flash plug 30 provides a seal 22 to separate chambers 28 and 21. When seal 22 is breached, vacuum within chamber 28 transfers to chamber 21 drawing fluid or gaseous substances through hollow bore needle 10 and into flashback chambers 21 and 28. The seal 22 may be breached by moving the flash plug 30 in a direction out of the needle hub 20.

Flash plug 30 sealingly engages needle hub 20 at section 40 even after seal 22 is broken and additional sub-atmospheric or hydraulic vacuum can be created within flashback chamber 21 by axially moving flash plug 30 farther away from needle 10. Flash plug 30 has an open proximal end and chamber 38. Flash plug 30 is removable from needle hub 20 and a syringe or the like can be attached to aspirate fluid or gaseous substances through or within the flashback chamber 21 and needle 10 if needed.

FIG. 19 is a full, cut away and cross sectional view of an I.V. catheter introduce that is slidably disposed on a hollow bore hypodermic needle (not shown) that is fixedly attached to needle hub 20. Needle hub 20 includes a flashback chamber 21. A flash plug 90 resides within needle hub 20. The hollow bore of the needle is connected to and in fluid communication with flashback chamber 21. Flash plug 90 is axially movable back and forth relative to hub 20.

Flash plug 90 sealingly engages the perimeter of flashback chamber 21 to create a contained space within needle hub 20. A separable, movable flash plug body 99 residing within flashback chamber 21 of needle hub 20 is movable axially or rotationally within chamber 21. Flash plug 90 sealingly engages inner wall section of flashback chamber 21. Flash plug 90 may also comprise an aperture or through hole 97 at the proximal, or external, end which acts as a vent connecting the flashback chamber 21 with the ambient atmosphere, flash plug 90 having porous membrane 96 residing within chamber 98 which allows gaseous substances to pass through, but substantially prevents fluids from passing through membrane 96.

The vent 97 allows air within flashback chamber 21 and plug chamber 98 to be expelled into the ambient atmosphere when blood enters flashback chamber 21 during normal catheter placement procedures. If blood fails to appear in chamber 21, the user can close or block vent 97 by placing a finger over the vent opening. The user may then slide the flash plug 90 away from the needle to create a sub-atmospheric, or negative, pressure within chamber 21 to aspirate blood through the needle and into chamber 21 and plug chamber 98.

Blood entering chamber 21 is a standard indicator that the distal end of catheter is residing within a blood vessel and is ready to be advanced. Porous membrane 96 is not necessary, but prevents blood from coming close to, or exiting, vent 97. Vent 97 can be manufactured small enough to allow air to escape when blood flows normally into chamber 98, but still prohibits blood from exiting vent 97. Negative pressure created within chambers 21 and 98 can be equalized by removing finger from vent 97 at any time during the suctioning process.

Flash plug 90 is removable from hub 20 allowing a syringe to be attached to the open end of chamber 21 to either create a suction within chamber 21 or to dispense fluid into chamber 21 and through attached, hollow bore needle (not shown).

FIG. 21 is a cross sectional view of one possible configuration of the external proximal section of flash plug shown in axis 21—21 having a substantially rectangular shape to allow easy placement of finger over vent. Any feasible shape is possible where user can open or block vent 97.

FIG. 20 is a full and cross sectional view of an I.V. catheter introducer in another embodiment having a separable catheter 13 connected to hub 12. The catheter being slidably disposed on a hypodermic needle (not shown). The hypodermic needle is fixedly attached to the needle hub 20 having flashback chamber 21. A flash plug 80 resides within needle hub 20 and is axially movable back or forth relative to introducer hub 20.

Flash plug 80 includes a plunger rod 85 with an attached piston 82 sealingly engaging the perimeter of flashback chamber 21 to create a contained space within needle hub 20. Flash plug 80 can be removed by gripping the proximal end 81 of the flash plug and moving the flash plug axially away from needle hub 20.

Flash plug 80 and piston 82 are removable from hub 20 allowing a syringe to be attached to the open end of chamber 21 to either create a suction within chamber 21 or to dispense fluid into chamber 21 and through attached, hollow bore needle (not shown). Piston 82 having a female section for insertion of distal male section 86 of plunger rod 85.

FIG. 22 is a cross sectional and cut away view of the present invention with the I.V. catheter introducer being ready to use, having a needle hub 20 with an aperture 26 corresponding with an aperture 77 of flash plug 70. The aperture or vent 77 is positioned on the body 79, rather than the proximal end, of flash plug 70 (as shown in FIG. 19). When flash plug 70 is fully inserted within flashback chamber 21, corresponding apertures 26 and 77 create access to chambers 78 and 21. Porous material 76 can be positioned in the flash plug chamber 78 between the aligned apertures and the hollow bore needle (not shown) which is connected to flashback chamber 21. If the initial veinipuncture is successful, blood freely flows through the hollow bore needle and into flashback chamber 21. Porous material 76 allows the air within flashback chamber 21 an unimpeded exit from flashback chamber 21, yet contains blood within chambers 21 and/or 78. If blood fails to flow into flash back chamber 21, axial movement of flash plug 70 away from needle hub 20 closes the vent produced by alignment of corresponding apertures 26 and 77, creating a negative, or sub-atmospheric pressure within flashback chamber 21 and/or flash plug chamber 78. If axial movement of flash plug 70 to close vent is not preferred, rotational movement will also close the vent.

FIG. 23 is a cross sectional view in axis 23—23 of the vent created by alignment of apertures 26 and 77 of FIG. 22. Axial, or rotational movement of flash plug 70 closes vent when apertures 26 and 77 no longer intersect.

Throughout the drawings, proximal end of the needle hub 20 can comprise an internal or external thread, or projection, for threadedly attaching flash plug 30, 70, 80, 90 or a syringe. Threaded means insures a positive axial position of flash plugs 30, 70, 80 or 90 along the length of chamber 21.

What is claimed is:

1. A system for introducing an intravenous catheter into a patient comprising:
   a needle having a proximal end and a distal end;
   a catheter tube slidably disposed over the needle;
   a needle hub, the proximal end of the needle secured within the needle hub;
   a flashback chamber having proximal and distal ends and an inner wall, the distal end of the flashback chamber being connected to the needle hub, the proximal end of the needle being in fluid communication with the distal end of the flashback chamber; and
   a flash plug sealingly engaged to and in fluid communication with the inner wall of said flashback chamber, said flash plug being transitionable between:
   i. a first non-operative configuration;
   ii. a second operative configuration wherein said flash plug controllably creates a vacuum in said flashback chamber; and
   wherein the flashback chamber and the flash plug each have an elliptical shape such that the rotation of the flash plug releases the sealing engagement of at least a portion of the flash plug with the inner wall of the flashback chamber.

2. The catheter of claim 1 further comprising venting means for venting the flashback chamber to the atmosphere.

3. The catheter of claim 2 further comprising an aperture providing an air flow passage between the internal chamber of the flash plug to the ambient atmosphere.

4. The catheter of claim 3 wherein the movement restricting means includes a projection on the flash plug that is engageable with a first recess in the inner wall of the flashback chamber.

5. The catheter of claim 2 further comprising a fluid absorbing member located in the internal chamber of the flash plug.

6. The catheter of claim 2 further comprising a second opening located at or near the proximal end of the flash plug and a porous membrane located in the internal chamber that allows gaseous substances to flow through the membrane and substantially prevents fluids from flowing through the membrane.

7. The catheter of claim 1 wherein the flash plug has a distal end and a proximal end, the distal end of the flash plug being proximal to the distal end of the flashback chamber when the flash plug is fully inserted into the flashback chamber, the flash plug having an internal chamber with an opening at the distal end of the flash plug.

8. The catheter of claim 1 wherein the flash plug further includes means for restricting the movement of the flash plug in a second direction from the proximal end to the distal end of the flashback chamber.

9. The catheter of claim 1 wherein the flash plug comprises a flange portion and a longitudinal body extending outwardly from the flange portion, the body being dimensioned smaller than the flashback chamber, the member comprising an elastomeric o-ring positioned on said body.

10. The catheter of claim 1 wherein the inner wall of the flashback chamber has a first section having a first diameter and a second section having a second diameter, the flash plug member having a third diameter, first diameter being substantially equal to or less than the third diameter, the second diameter being greater than the third diameter.

11. The catheter of claim 1 wherein the flash plug has a distal end and a proximal end, the distal end of the flash plug being proximal to the distal end of the flashback chamber when the flash plug is fully inserted into the flashback chamber, the flash plug having an internal chamber at a sub-atmospheric pressure, the distal end of the flash plug being piercable by the proximal end of the needle when the flash plug is fully inserted into the flashback chamber.

12. The catheter of claim 1 wherein the flash plug has a distal end and a proximal end, the distal end of the flash plug being proximal to the distal end of the flashback chamber when the flash plug is fully inserted into the flashback chamber, the flash plug having an internal chamber with a first opening at the distal end of the flash plug and a second opening at the proximal end of the flash plug, a removable end cap in sealing engagement with the second opening.

13. The catheter of claim 1 wherein the member is movable within the flashback chamber in a second direction from the proximal end to the distal end of the flashback chamber.

14. A system for introducing an intravenous catheter into a patient comprising:
- a needle having a proximal end and a distal end;
- a catheter tube slidably disposed over the needle;
- a needle hub, the proximal end of the needle secured within the needle hub;
- a flashback chamber having a proximal end, a distal end and an inner wall, the distal end of the flashback chamber being connected to the needle hub, the proximal end o the needle being in fluid communication with the distal end of the flashback chamber; and
- a flash plug sealingly engaged to and in fluid communication with the inner wall of said flashback chamber, said flash plug being transitionable between:
  i. a first non-operative configuration;
  ii. a second operative configuration wherein said flash plug controllably creates a vacuum in said flashback chamber; and
- wherein the flashback chamber and the flash plug each have an elliptical shape such that the rotation of the flash plug releases the sealing engagement of at least a portion of the flash plug with the inner wall of the flashback chamber.

15. A method for drawing blood into a flashback chamber of an intravenous catheter comprising the steps:
a) providing a system for introducing an intravenous catheter, said system comprising a needle having a proximal end and a distal end, a catheter tube slidably disposed over the needle, a needle hub, the proximal end of the needle secured within the needle hub, a flashback chamber having a proximal end, a distal end and an inner wall, the distal end of the flashback chamber being connected to the needle hub, the proximal end of the needle being in fluid communication with the distal end of the flashback chamber, and a flash plug sealingly engaged to and in fluid communication with said flashback chamber, said flash plug being transitionable between:
  i. a first non-operative configuration;
  ii. a second operative configuration wherein said flash plug controllably creates a vacuum in said flashback chamber; and
- wherein the flashback chamber and the flash plug each have an elliptical shape such that the rotation of the flash plug releases the sealing engagement of at least a portion of the flash plug with the inner wall of the flashback chamber;
b) introducing the distal end of the needle into a vein; and
c) causing said flash plug to transition from said non-operative configuration to said operative configuration.

16. A method for drawing blood into a flashback chamber of an intravenous catheter comprising the steps:
a) providing a system for introducing an intravenous catheter, said system comprising a needle having a proximal end and a distal end, a catheter tube slidably disposed over the needle, a needle hub, the proximal end of the needle secured within the needle hub, a flashback chamber having a proximal end, a distal end and an inner wall, the distal end of the flashback chamber being connected to the needle hub, the proximal end of the needle being in fluid communication with the distal end of the flashback chamber, and a flash plug sealingly engaged to and in fluid communication with said flashback chamber, said flash plug being transitionable between:
  i. a first non-operative configuration;
  ii. a second operative configuration wherein said flash plug controllably creates a vacuum in said flashback chamber; and
- wherein the flashback chamber and the flash plug each have an elliptical shape such that the rotation of the flash plug releases the sealing engagement of at least a portion of the flash plug with the inner wall of the flashback chamber;
b) introducing the distal end of the needle into a portion of a body having a vein;
c) causing said flash plug to transition from said non-operative configuration to said operative configuration; and
d) introducing the distal end of the needle into the vein.

17. A system for introducing and intravenous catheter into a patient comprising:
(a) a needle having a proximal end and a distal end;
(b) a catheter tube slidably disposed over the needle;
(c) a needle hub, the proximal end of the needle secured within the needle hub;
(d) a flashback chamber having a proximal and distal ends and an inner wall, the distal end of the flashback chamber being connected to the needle and, the proximal end of the needle being in fluid communication with the distal end of the flashback chamber;
(e) a flash plug sealingly engaged with the inner wall of the flashback chamber, the flash plug being moveable within the flashback chamber in a first direction from a distal end to the proximal end of the flashback chamber, movement of the flash plug in the first direction creating a vacuum in the flashback chamber; and
(f) wherein the flash plug has a distal end and a proximal end, the distal end of the flash plug being proximal to the distal end of the flashback chamber when the flash plug is fully inserted into the flashback chamber, the flash plug having an internal chamber with an opening at the distal end of the flash plug, said internal chamber having a movable diaphragm located therewithin.

18. A method for drawing blood into a flashback chamber an intravenous catheter, the intravenous catheter comprising of a needle having a proximal end and a distal end, a catheter tube slidably disposed over the needle, a needle hub having a proximal end of the needle secured therewithin, a flashback chamber having proximal and distal ends in an inner wall, the distal end of the flashback chamber being connected to the needle hub and the proximal end of the needle being in fluid communication with the distal end of the flashback chamber, and a flash plug sealingly engaged with the inner wall of the flashback chamber, the flash plug having a distal end and a proximal end and oriented such that the distal end of the flash plug is proximal to the distal end of the flashback chamber, the flash plug being movable within the flashback chamber in a first direction from a distal end to the proximal end of the flashback chambers such that movement of the flash plug in the first direction creates a vacuum in the flashback chamber, the flash plug further having an internal chamber with an opening of the distal end thereof, said internal chamber having a movable diaphragm located therewithin:
a) introducing the distal end of the needle into a vein; and
b) moving the flash plug in said direction to create a vacuum in the flashback chamber.

* * * * *